(12) United States Patent
Cohen et al.

(10) Patent No.: US 8,604,268 B2
(45) Date of Patent: Dec. 10, 2013

(54) SENSOR AND ASSOCIATED ARTICLES FOR TOILET TRAINING

(75) Inventors: Jason C. Cohen, Appleton, WI (US);
Thomas M. Ales, III, Neenah, WI (US);
Shirlee A. Weber, Neenah, WI (US);
Andrew M. Long, Appleton, WI (US);
Christopher P. Olson, Neenah, WI (US); Ansley Allen, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1570 days.

(21) Appl. No.: 11/540,418

(22) Filed: Sep. 29, 2006

(65) Prior Publication Data

US 2008/0082062 A1  Apr. 3, 2008

(51) Int. Cl.
*A61F 13/15* (2006.01)

(52) U.S. Cl.
USPC ........................................................ 604/361

(58) Field of Classification Search
USPC ........................................................ 604/361
See application file for complete search history.

(56) References Cited

U.S. PATENT DOCUMENTS

| | | | |
|---|---|---|---|
| 4,162,490 A | 7/1979 | Fu et al. | |
| 4,704,116 A | 11/1987 | Enloe | |
| 4,768,023 A | 8/1988 | Xie | |
| 4,798,603 A | 1/1989 | Meyer et al. | |
| 4,820,164 A | 4/1989 | Kemper | |
| 4,940,464 A | 7/1990 | Van Gompel et al. | |
| 5,008,964 A | 4/1991 | Dean et al. | |
| 5,176,672 A | 1/1993 | Bruemmer et al. | |
| 5,264,830 A | 11/1993 | Kline et al. | |
| 5,395,358 A | 3/1995 | Lu | |
| 5,469,145 A | 11/1995 | Johnson | |
| 5,486,166 A | 1/1996 | Bishop et al. | |
| 5,490,846 A | 2/1996 | Ellis et al. | |
| 5,509,915 A | 4/1996 | Hanson et al. | |
| 5,560,051 A | 10/1996 | Butts | |
| 5,568,128 A | 10/1996 | Nair | |
| 5,573,407 A | 11/1996 | Dunford | |
| 5,725,382 A | 3/1998 | Walter et al. | |
| 5,766,389 A | 6/1998 | Brandon et al. | |
| 5,796,345 A | 8/1998 | Leventis et al. | |
| 5,817,076 A | 10/1998 | Fard | |
| 5,820,973 A | 10/1998 | Dodge, II et al. | |
| 5,868,723 A | 2/1999 | Al Sabah | |
| 5,908,411 A | 6/1999 | Matsunari | |
| 5,978,976 A | 11/1999 | Chai | |
| 5,993,433 A | 11/1999 | St. Louis et al. | |

(Continued)

FOREIGN PATENT DOCUMENTS

WO    WO 00/37009 A2    6/2000
WO    WO 2007/125483 A1    11/2007

*Primary Examiner* — Lynne Anderson
(74) *Attorney, Agent, or Firm* — Kimberly-Clark Worldwide, Inc.

(57) ABSTRACT

Presented is a toilet training system including a disposable absorbent article including a first wetness sensor; a first signaling device adapted to communicate with the first wetness sensor and providing a first feedback mode of a wetness state of the disposable absorbent article; and a second signaling device adapted to communicate with the first wetness sensor and providing a second feedback mode of the wetness state of the disposable absorbent article, wherein the second feedback mode is different from the first feedback mode. Also presented is a toilet training system including a disposable absorbent article including a wetness sensor; and a signaling device adapted to communicate with the wetness sensor, wherein the signaling device includes a dynamic feedback mode system.

19 Claims, 1 Drawing Sheet

(56) References Cited

U.S. PATENT DOCUMENTS

| | | | |
|---|---|---|---|
| 6,093,869 A | 7/2000 | Roe et al. | |
| 6,101,366 A | 8/2000 | Castillo | |
| 6,149,636 A | 11/2000 | Roe et al. | |
| 6,175,310 B1 * | 1/2001 | Gott | 340/605 |
| 6,186,991 B1 | 2/2001 | Roe et al. | |
| 6,200,250 B1 | 3/2001 | Janszen | |
| 6,246,330 B1 | 6/2001 | Nielsen | |
| 6,248,097 B1 | 6/2001 | Beitz et al. | |
| 6,250,929 B1 | 6/2001 | Kolb et al. | |
| 6,384,296 B1 | 5/2002 | Roe et al. | |
| 6,417,455 B1 | 7/2002 | Zein et al. | |
| 6,433,244 B1 | 8/2002 | Roe et al. | |
| 6,570,053 B2 | 5/2003 | Roe et al. | |
| 6,617,488 B1 | 9/2003 | Springer et al. | |
| 6,635,797 B2 * | 10/2003 | Olson et al. | 604/361 |
| 6,645,190 B1 | 11/2003 | Olson et al. | |
| 6,658,432 B1 | 12/2003 | Warikoo et al. | |
| 6,677,859 B1 | 1/2004 | Bensen | |
| 6,772,454 B1 | 8/2004 | Barry et al. | |
| 6,791,004 B2 | 9/2004 | Sprengard Eichel et al. | |
| 6,970,091 B2 | 11/2005 | Roe | |
| 7,295,125 B2 * | 11/2007 | Gabriel | 340/604 |
| 7,355,090 B2 | 4/2008 | Ales, III et al. | |
| 7,498,478 B2 | 3/2009 | Long et al. | |
| 2002/0021220 A1 * | 2/2002 | Dreyer | 340/573.1 |
| 2002/0070868 A1 | 6/2002 | Jeutter et al. | |
| 2003/0123330 A1 | 7/2003 | Carter et al. | |
| 2004/0018474 A1 | 1/2004 | D'Ippolito | |
| 2004/0064113 A1 | 4/2004 | Erdman | |
| 2004/0064114 A1 | 4/2004 | David et al. | |
| 2004/0113801 A1 | 6/2004 | Gustafson et al. | |
| 2004/0207530 A1 | 10/2004 | Nielsen | |
| 2004/0220538 A1 | 11/2004 | Panopoulos | |
| 2004/0236302 A1 | 11/2004 | Wilhelm et al. | |
| 2004/0254549 A1 | 12/2004 | Olson et al. | |
| 2005/0064377 A1 | 3/2005 | Whitfield | |
| 2005/0065489 A1 | 3/2005 | Driskell et al. | |
| 2005/0110644 A1 | 5/2005 | Abramson et al. | |
| 2005/0137542 A1 | 6/2005 | Underhill et al. | |
| 2005/0239029 A1 | 10/2005 | Yzermans et al. | |
| 2005/0245839 A1 | 11/2005 | Stivoric et al. | |
| 2007/0049881 A1 | 3/2007 | Ales et al. | |
| 2007/0142797 A1 | 6/2007 | Long et al. | |
| 2007/0142799 A1 | 6/2007 | Ales et al. | |
| 2007/0252712 A1 | 11/2007 | Allen et al. | |

* cited by examiner

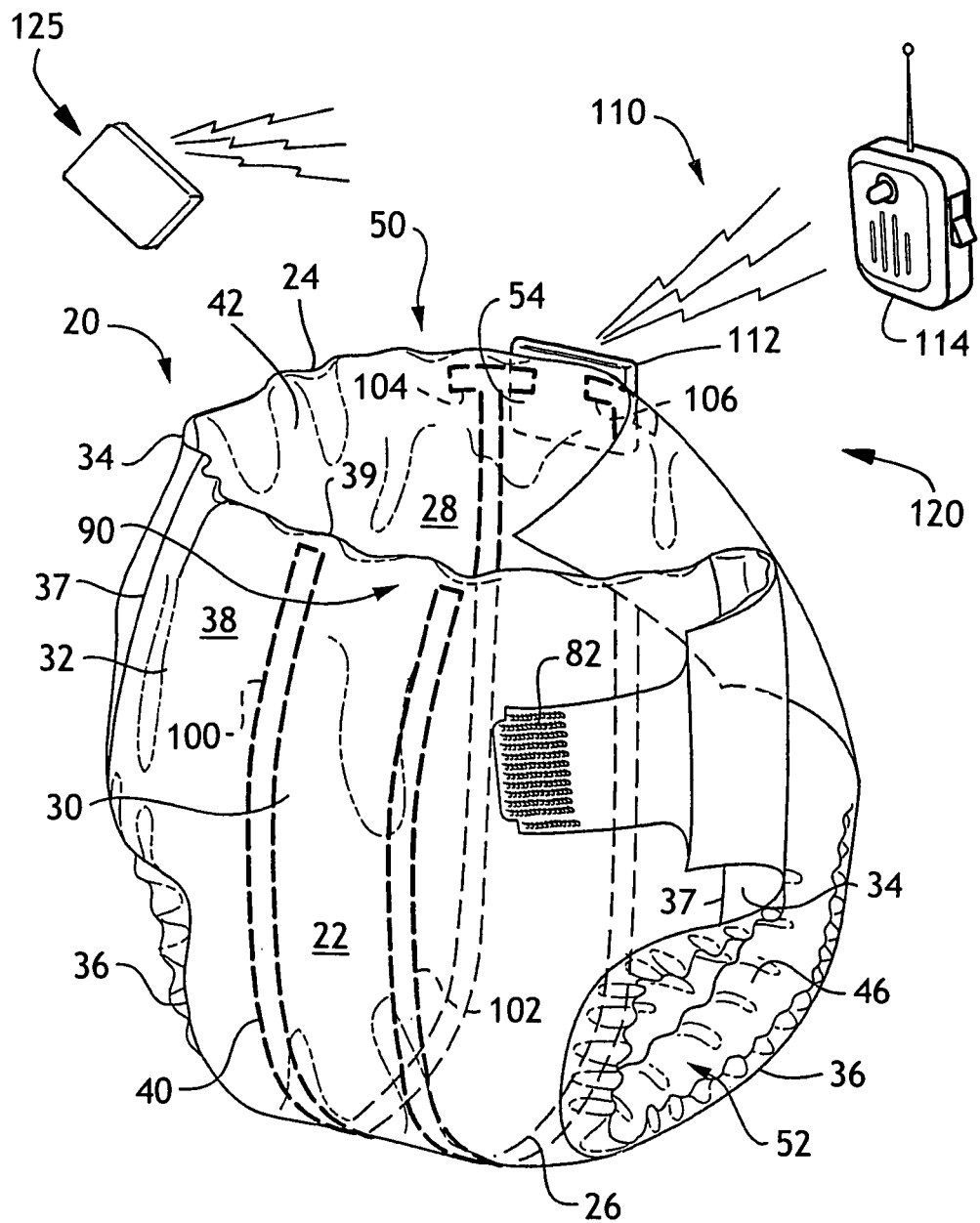

SENSOR AND ASSOCIATED ARTICLES FOR TOILET TRAINING

BACKGROUND OF THE INVENTION

Absorbent articles such as diapers, training pants, incontinence products, feminine hygiene products, swim undergarments, and the like conventionally include a liquid permeable body-side liner, a liquid impermeable outer cover, and an absorbent core. The absorbent core is typically located in between the outer cover and the liner for taking in and retaining liquids (e.g., urine) exuded by the wearer.

Many absorbent articles have been adapted for use in a training program, such as toilet training or enuresis control, or to provide indication of various medical, physical, or other conditions. Accordingly, various types of sensors and indicators, including moisture or wetness indicators, have been suggested for use in absorbent articles. Wetness indicators, for example, may include alarm devices that are designed to assist parents or attendants to identify a wet diaper condition quickly upon insult. The devices produce either a visual or an audible signal.

Problems, however, have been encountered in using such articles for training and/or notification purposes in that current training aids provide feedback to either the caregiver or user when an event occurs. This feedback is consistent and does not vary/adjust as a function of training time or as a function of training needs based on trending success or failure. An additional concern with constant training feedback (e.g., always a musical tone) is that the individuals can habituate to the type of feedback signal.

SUMMARY OF THE INVENTION

As caregivers undertake training, indication, and/or notification programs to address toilet training, enuresis control, incontinence monitoring, or condition monitoring, which apply across demographics, those caregivers would benefit by gaining greater access to products and guidance that are specifically designed to enhance the effectiveness of such programs.

The invention described herein solves the problems described above and provides an increase in efficacy in using wetness and other sensors in absorbent articles. In general, the present disclosure is directed to sensing absorbent articles with easy-to-use signaling devices. The signaling device, for instance, may be configured to indicate to a user that a body fluid is present in the sensing absorbent article.

For example, in one aspect of the present invention, the invention includes a toilet training system including a disposable absorbent article including a first wetness sensor; a first signaling device adapted to communicate with the first wetness sensor and providing a first feedback mode of a wetness state of the disposable absorbent article; and a second signaling device adapted to communicate with the first wetness sensor and providing a second feedback mode of the wetness state of the disposable absorbent article, wherein the second feedback mode is different from the first feedback mode.

In another aspect of the present invention, the invention includes a toilet training system including a disposable absorbent article including a wetness sensor; and a signaling device adapted to communicate with the wetness sensor, wherein the signaling device includes a dynamic feedback mode system.

BRIEF DESCRIPTION OF THE DRAWINGS

The foregoing and other features and aspects of the present invention and the manner of attaining them will become more apparent, and the invention itself will be better understood by reference to the following description, appended claims and accompanying drawings, where:

FIG. 1 is a perspective view of an absorbent article of the present invention.

Repeat use of reference characters in the present specification and drawings is intended to represent the same or analogous features or elements of the present invention. The drawings are representational and are not necessarily drawn to scale. Certain proportions thereof may be exaggerated, while others may be minimized.

DETAILED DESCRIPTION OF THE INVENTION

It is to be understood by one of ordinary skill in the art that the present discussion is a description of exemplary aspects of the present invention only, and is not intended as limiting the broader aspects of the present invention.

The present disclosure is generally directed to sensing absorbent articles adapted to be attached to a signaling device that may be configured to indicate the presence of a body fluid in the absorbent article or other changes in the condition of the product or wearer. The absorbent article may be, for instance, a diaper, a training pant, a pre-fastened pant, a swimming pant, an incontinence product, a feminine hygiene product, a medical garment, a bandage, or any other suitable article.

The invention described herein may be used with any type of sensing article. In one type of sensing article used as a non-limiting example herein, wetness sensing absorbent articles may include an open circuit that becomes closed when a conductive fluid, such as a body fluid, is present in between a pair of conductive leads. Alternatively, wetness sensing absorbent articles may include a closed circuit that becomes open when a fluid, such as a body fluid, is present. Generally, the wetness sensing absorbent articles containing the circuit are disposable, meaning that they are designed to be discarded after a limited use rather than being laundered or otherwise restored for reuse.

The circuit contained within the wetness sensing absorbent articles of the present disclosure is configured to be attached to a signaling device. The signaling device can provide power to the circuit while also including some type of audible, visible, tactile, and/or electromagnetic signal that indicates to the user the presence of a body fluid. Although the wetness sensing absorbent article may itself be disposable, the signaling device may be reusable from article to article. In this regard, the present disclosure is particularly directed to different types of attachment modes that allow easy connection between the circuit in the wetness sensing absorbent article and the signaling device.

As described above, the circuit in combination with the signaling device may be configured to indicate the presence of a body fluid contained within the wetness sensing absorbent article. The particular targeted body fluid may vary depending upon the particular type of wetness sensing absorbent article and the desired application. For instance, in one aspect of the present invention, the wetness sensing absorbent article comprises a diaper, a training pant, or the like and the signaling device is configured to indicate the presence of urine. Alternatively, the signaling device may be configured to indicate the presence of a metabolite that would indicate the presence of a diaper rash. For adult incontinence products and feminine hygiene products, on the other hand, the signaling device may be configured to indicate the presence of a yeast or of a particular constituent in urine or menses, such as a polysaccharide, a sugar, a protein, etc.

Referring to FIG. 1, for non-limiting exemplary purposes, a wetness sensing absorbent article 20 is shown. The wetness sensing absorbent article 20 may or may not be disposable. It is understood that the present invention is suitable for use with various other wetness sensing absorbent articles intended for personal wear, including but not limited to diapers, training pants, swim pants, feminine hygiene products, incontinence products, medical garments, surgical pads and bandages, other personal care or health care garments, and the like without departing from the scope of the present invention.

By way of illustration only, various materials and methods for constructing wetness sensing absorbent articles such as the wetness sensing absorbent article 20 of the various aspects of the present invention are disclosed in U.S. Pat. No. 4,798,603 issued Jan. 17, 1989, to Meyer et al.; U.S. Pat. No. 5,176,672 issued Jan. 5, 1993, to Bruemmer et al., U.S. Pat. No. 5,509,915 issued Apr. 23, 1996, to Hanson et al., U.S. Pat. No. 5,993,433 issued Nov. 30, 1999, to St. Louis et al., and U.S. Pat. No. 6,248,097 issued Jun. 19, 2001, to Beitz et al., PCT Patent Application WO 00/37009 published Jun. 29, 2000, by A. Fletcher et al; U.S. Pat. No. 4,940,464 issued Jul. 10, 1990, to Van Gompel et al.; U.S. Pat. No. 5,766,389 issued Jun. 16, 1998, to Brandon et al., and U.S. Pat. No. 6,645,190 issued Nov. 11, 2003, to Olson et al., which are incorporated herein by reference to the extent they are consistent (i.e., not in conflict) herewith.

A wetness sensing absorbent article 20 is representatively illustrated in FIG. 1 in a partially fastened condition.

The wetness sensing absorbent article 20 defines a pair of longitudinal end regions, otherwise referred to herein as a front region 22 and a back region 24, and a center region, otherwise referred to herein as a crotch region 26, extending longitudinally between and interconnecting the front and back regions 22, 24. The wetness sensing absorbent article 20 also defines an inner surface 28 adapted in use (e.g., positioned relative to the other components of the article 20) to be disposed toward the wearer, and an outer surface 30 opposite the inner surface. The front and back regions 22, 24 are those portions of the wetness sensing absorbent article 20, which when worn, wholly or partially cover or encircle the waist or mid-lower torso of the wearer. The crotch region 26 generally is that portion of the wetness sensing absorbent article 20 which, when worn, is positioned between the legs of the wearer and covers the lower torso and crotch of the wearer. The wetness sensing absorbent article 20 has a pair of laterally opposite side edges 36 and a pair of longitudinally opposite waist edges, respectively designated front waist edge 38 and back waist edge 39.

The illustrated wetness sensing absorbent article 20 includes a chassis 32 that, in this aspect of the present invention, encompasses the front region 22, the back region 24, and the crotch region 26. The chassis 32 includes an outer cover 40 and a bodyside liner 42 that may be joined to the outer cover 40 in a superimposed relation therewith by adhesives, ultrasonic bonds, thermal bonds or other conventional techniques. The liner 42 can be generally adapted, i.e., positioned relative to the other components of the article 20, to be disposed toward the wearer's skin during wear of the wetness sensing absorbent article. The chassis 32 may further include an absorbent structure (not shown) disposed between the outer cover 40 and the bodyside liner 42 for absorbing liquid body exudates exuded by the wearer, and may further include a pair of containment flaps 46 secured to the bodyside liner 42 for inhibiting the lateral flow of body exudates. Suitable constructions and arrangements for the containment flaps 46 are generally well known to those skilled in the art and are described in U.S. Pat. No. 4,704,116 issued Nov. 3, 1987, to Enloe, which is incorporated herein by reference.

To further enhance containment and/or absorption of body exudates, the wetness sensing absorbent article 20 may also suitably include leg elastic members (not shown), as are known to those skilled in the art.

In some aspects of the present invention, the wetness sensing absorbent article 20 may further include a surge management layer (not shown) which may be optionally located adjacent the absorbent structure and attached to various components in the article 20 such as the absorbent structure or the bodyside liner 42 by methods known in the art, such as by using an adhesive. A surge management layer helps to decelerate and diffuse surges or gushes of liquid that may be rapidly introduced into the absorbent structure of the article. Desirably, the surge management layer can rapidly accept and temporarily hold the liquid prior to releasing the liquid into the storage or retention portions of the absorbent structure. Examples of suitable surge management layers are described in U.S. Pat. Nos. 5,486,166; and 5,490,846. Other suitable surge management materials are described in U.S. Pat. No. 5,820,973. The entire disclosures of these patents are hereby incorporated by reference herein to the extent they are consistent (i.e., not in conflict) herewith.

As shown in FIG. 1, the wetness sensing absorbent article 20 further includes a pair of opposing elastic side panels 34 that are attached to the back region of the chassis 32. As shown particularly in FIG. 1, the side panels 34 may be stretched around the waist and/or hips of a wearer to secure the garment in place. The elastic side panels are attached to the chassis along a pair of opposing longitudinal edges 37. The side panels 34 may be attached or bonded to the chassis 32 using any suitable bonding technique. For instance, the side panels 34 may be joined to the chassis by adhesives, ultrasonic bonds, thermal bonds, or other conventional techniques. Ultimately, the side panels 34 are generally aligned with a waist region 90 of the chassis.

In an alternative aspect of the present invention, the elastic side panels may also be integrally formed with the chassis 32. For instance, the side panels 34 may comprise an extension of the bodyside liner 42, of the outer cover 40, or of both the bodyside liner 42 and the outer cover 40.

The side panels 34 are connected to the back region of the wetness sensing absorbent article 20 and extend over the front region of the article when securing the article in place on a user. It should be understood, however, that the side panels 34 may alternatively be connected to the front region of the article 20 and extend over the back region when the article is donned.

With the wetness sensing absorbent article 20 in the fastened position as partially illustrated in FIG. 1, the elastic side panels 34 may be connected by a fastening system 82 to define a 3-dimensional wetness sensing absorbent article configuration having a waist opening 50 and a pair of leg openings 52. The waist opening 50 of the article 20 is defined by the waist edges 38 and 39 which encircle the waist of the wearer.

In the aspects of the present invention shown in the figures, the side panels are releasably attachable to the front region 22 of the article 20 by the fastening system 82. It should be understood, however, that in other aspects of the present invention the side panels may be permanently joined to the chassis 32 at each end. The side panels may be permanently bonded together, for instance, when forming a training pant or absorbent swimwear.

The fastening system 82 may include laterally opposite first fastening components adapted for refastenable engagement to corresponding second fastening components. The fastening system 82 may include any refastenable fasteners suitable for wetness sensing absorbent articles, such as adhesive fasteners, cohesive fasteners, mechanical fasteners, or the like. In particular aspects, the fastening components include mechanical fastening elements for improved performance. Suitable mechanical fastening elements can be provided by interlocking geometric shaped materials, such as hooks, loops, bulbs, mushrooms, arrowheads, balls on stems, male and female mating components, buckles, snaps, or the like. Suitable fastening systems are also disclosed in the previously incorporated PCT Patent Application WO 00/37009 published Jun. 29, 2000, by A. Fletcher et al. and the previously incorporated U.S. Pat. No. 6,645,190 issued Nov. 11, 2003, to Olson et al.

In addition to possibly having elastic side panels, the wetness sensing absorbent article 20 may include various waist elastic members for providing elasticity around the waist opening. For example, as shown in the figures, the wetness sensing absorbent article 20 can include a front waist elastic member 54 and/or a back waist elastic member (not shown).

As described above, the present disclosure is particularly directed to incorporating a wetness sensor. One such sensor is described below. Other sensors include a wetness liner such as that described in U.S. Pat. No. 6,658,432 to Underhill et al., a temperature system, a system in which graphics fade or appear, and any other suitable wetness sensor.

One such wetness sensor is the wetness indicating system described herein. In this regard, as shown in FIG. 1, the wetness sensing absorbent article 20 includes a first conductive element 100 spaced from a second conductive element 102. In this aspect of the present invention, the conductive elements extend from the front region 22 of the wetness sensing absorbent article to the back region 24 without intersecting. The conductive elements 100 and 102 can comprise any suitable conductive material, such as a conductive thread or a conductive foil for example include 112-S silver metallic conductive paste (ink) from Electroscience Laboratories, Inc. and conductive foil described in U.S. Pat. No. 6,417,455 issued Jul. 9, 2002, to Zein et. Al. The first conductive element 100 may not intersect the second conductive element 102 in order to form an open circuit that may be closed, for instance, when a conductive fluid is positioned in between the conductive elements. In other aspects of the present invention, however, the first conductive element 100 and the second conductive element 102 may be connected to a sensor within the chassis. The sensor may be used to sense changes in temperature or may be used to sense the presence of a particular substance, such as a metabolite.

In the aspect of the present invention shown in FIG. 1, the conductive elements 100 and 102 extend the entire length of the wetness sensing absorbent article 20. It should be understood, however, that in other aspects of the present invention the conductive elements may extend only to the crotch region 26 or may extend to any particular place in the wetness sensing absorbent article where a body fluid is intended to be sensed.

The conductive elements 100 and 102 may be incorporated into the chassis 32 at any suitable location as long as the conductive elements are positioned so as to contact a body fluid that is absorbed by the wetness sensing absorbent article 20. In this regard, the conductive elements 100 and 102 generally lie inside the outer cover 40. In fact, in one aspect of the present invention, the conductive elements 100 and 102 may be attached or laminated to the inside surface of the outer cover 40 that faces the absorbent structure. Alternatively, however, the conductive elements 100 and 102 may be positioned on the absorbent structure or positioned on the liner 42.

The conductive element 100 and 102 may be connected directly to a signaling device, either through direct or indirect contact. The first conductive element 100 may be attached to a first conductive pad member 104, while the second conductive element 102 may be connected to a second conductive pad member 106. The pad members 104 and 106 may be provided for making a reliable connection between the open circuit formed by the conductive elements to a signaling device that is intended to be installed on the chassis by the consumer or manufacturer. The pad members 104 and 106 may create a zone for connecting the signaling device and the conductive leads or elements.

The conductive pad members 104 and 106 may have a relatively large surface area in relation to the conductive elements 100 and 102. For example, the conductive pad members 104 and 106 may have a surface area of at least 0.5 $cm^2$, at least 1 $cm^2$, at least 2 $cm^2$, and, in another aspect of the present invention, at least 3 $cm^2$. For instance, in another aspect of the present invention, the surface area of each pad member may be from about 2 $cm^2$ to about 4 $cm^2$.

The position of the conductive pad members 104 and 106 on the wetness sensing absorbent article 20 can vary depending upon where it is desired to mount the signaling device. For instance, in FIG. 1, the conductive pad members 104 and 106 are positioned in the back region 24 along the waist opening 50 of the article. In another aspect of the present invention that is not shown, the conductive pad members 104 and 106 are positioned in the front region 22 along the waist opening 50 of the article. It should be appreciated, however, that in other aspects of the present invention, the wetness sensing absorbent article 20 may include conductive pad members being positioned at each end of each conductive element 100 and 102. In still other aspects of the present invention, it should be understood that the pad members may be located along the side of the article or towards the crotch region of the article.

The position of the conductive pad members 104 and 106 within the multiple layers of the chassis 32 may also vary depending upon where it is desired to connect the signaling device and the type of attachment mode used to make a connection with the signaling device. As described above, the pad members 104 and 106 are electrically connected to the conductive elements 100 and 102. Thus, in one aspect of the present invention, the pad members 104 and 106 are positioned below (toward the body side) at least one layer of the outer cover 40. Positioning the pad members 104 and 106 below at least one layer of material may provide, various advantages in some aspects of the present invention. For instance, locating the pad members 104 and 106 below at least one layer of material within the chassis 32 protects the pad members during shipping and storage and from forming a short circuit during use especially if the pad members are located adjacent one another. Another benefit to placing the pad members under at least one layer of material is the ability to easily manufacture the wetness sensing absorbent article 20 at high machine speeds.

It should be understood, however, that in other aspects of the present invention the conductive pad members 104 and 106 may be positioned at an exterior surface of the chassis 32. For instance, the pad members 104 and 106 may be positioned on the outside surface or on the inside surface as desired.

Further details related to the structure, features, and materials of the absorbent article 20 may be found in co-pending and co-assigned U.S. patent application Ser. No. 11/414,032, filed on Apr. 27, 2006, by Allen, et al. and entitled "An Array of Wetness Sensing Articles," which is incorporated herein by reference to the extent it is consistent (i.e., not in conflict) herewith.

Referring to FIG. 1 for exemplary purposes, a signaling device 110 (as depicted by ref. numerals 112 and 114) is shown attached to the conductive pad members 104 and 106. As shown, in this aspect of the present invention, the signaling device generally 110 includes a transmitter 112 and a receiver 114. The transmitter 112 includes a pair of opposing terminals that are electrically connected to the corresponding conductive elements. When a body fluid is present in the wetness sensing absorbent article 20, the open circuit formed by the conductive elements 100 and 102 is closed which, in turn, activates the signaling device 110. In particular, in this aspect of the present invention, the transmitter 112 sends a wireless signal to the receiver 114 which then indicates to a user that a body fluid is present in the wetness sensing absorbent article 20. In other various aspects of the present invention, any chemical or physical reaction that can change conductivity can also be sensed by this type of system—examples include conductivity changes associated with electrochemical sensors inside of the absorbent article 20 such as those described in co-pending and co-assigned U.S. patent application Ser. No. 11/314,438, filed on Dec. 21, 2005, by Ales et al. and entitled "Personal Care Products with Microchemical Sensors for Odor Detection," which is incorporated herein by reference to the extent it is consistent (i.e., not in conflict) herewith.

The signaling device 110 can emit an audible signal or a visual signal to indicate to the user that the circuit has been closed. The audible signal, for instance, may be as simple as one or more beeps to perhaps emitting a musical tune. Similarly, if the signaling device 110 issues a visible signal, the visible signal may comprise one light, a few lights, or an interactive display. In still another aspect of the present invention, the receiver 114 of the signaling device 110 may be configured to vibrate when the circuit within the wetness sensing absorbent article is closed.

In the aspect of the present invention shown in FIG. 1, the signaling device 110 includes a transmitter 112 in combination with a receiver 114. It should also be understood, however, that the signaling device may comprise a single unit that remains attached to the wetness sensing absorbent article 20. For example, the signaling device may be mounted on the wetness sensing absorbent article and issue a visible signal and/or an audible signal from the article itself.

In various aspects of the present invention, the wetness sensing absorbent article 20 may include additional features such as those disclosed in co-pending and co-assigned U.S. patent application Ser. No. 11/303,283 to Long, et al. and entitled "Garments With Easy-To-Use Signaling Device"; and U.S. patent application Ser. No. 11/215,937 to Ales, et al. and entitled "Method of Detecting the Presence of an Insult in an Absorbent Article and Device for Detecting the Same"; which are incorporated herein by reference to the extent they are consistent (i.e., not in conflict) herewith. For example, the wetness sensing absorbent article may also include other wetness sensing features such as fading ink, appearing ink, a wetness liner, or a cooling component.

The wetness sensing absorbent article 20 may be a part of a wetness sensing or body fluid indicating system 120 such as those described in above-referenced co-pending and co-assigned U.S. patent application Ser. No. 11/414,032, filed on Apr. 27, 2006, by Allen, et al. and entitled "An Array of Wetness Sensing Articles."

In various aspects of the present invention, the toilet training system described herein includes an available variety of indicating, signal-generating, and feedback modes (collectively called feedback modes or indications) to help a caregiver and subject avoid accustomization to a single signal or other feedback mode. The variety of feedback modes may be available in a single signaling device 110, or in a plurality of signaling devices 110, or both.

The wetness sensing absorbent article 20 may be a part of a wetness sensing system 120. In one aspect of the present invention, the wetness sensing system 120 includes a wetness sensing absorbent article 20, a first signaling device 110 that is compatible with the wetness sensing absorbent article 20, and a second signaling device 125 that is also compatible with the wetness sensing absorbent article 20. The wetness sensing system 120 may also include a receiver 114. In various aspects of the present invention, the wetness sensing absorbent article 20 may be configured to be used in toilet training a child, in addressing enuresis in a subject, or in monitoring incontinence in a subject, particularly an adult. In one aspect of the present invention, each signaling device manufactured and sold will be compatible with every wetness sensing absorbent article manufactured and sold for any application.

In various aspects of the present invention, a first signaling device 110 and a second signaling device 125 may both be manufactured and offered for sale. In one aspect, the first signaling device 110 may produce a first sound, and the second signaling device 125 may produce a second sound, where the first sound is different from the second sound. For example, the first signaling device 110 may produce a popular children's song, while the second signaling device 125 produces a beeping sound.

In various aspects of the present invention, the signaling device 110 includes features beyond those in the more basic signaling devices described above. In one aspect, the signaling device 110 produces a plurality of signals. For example, the signaling device 110 may produce a plurality of sounds, including, for example, a plurality of songs. In another example, the signaling device 110 may produce a plurality of tactile signals. In another example, the signaling device 110 may produce a plurality of wireless signals. In another example, the signaling device 110 may produce a combination of these feedback modes.

In another aspect of the present invention, the signaling device 110 may be adapted by any suitable means such that the user may select among a plurality of feedback modes. This is useful, for example, in a situation where a subject has grown accustomed to one feedback mode such as singing along with a song-type signal rather than responding to the song-type signal in a training capacity. The caregiver can select a different signal to continue the training. In a further aspect of the present invention, the signal may be switched off, for example, to silence an alarm or to preserve battery life.

In another aspect of the present invention, the plurality of signals in the signaling device 110 may include a combination of sounds and wireless signals. This is useful, for example, when the caregiver wants to select a first signal in the form of a sound for use in toilet training a child in the home, but a second signal in the form of a wireless signal for use in toilet training the child when in public, to avoid the stigma of a publicly-audible wetness alarm.

In another aspect of the present invention, the signaling device 110 is adapted by any suitable means to accept sounds or other information downloaded via computer, cell phone, or other device or means. Furthermore, this downloaded information may be downloaded or programmed into the signaling device 110 and be customized to the circumstances of the caregiver and/or subject. This customization may be based on feedback solicited from the caregiver (on frequency of wetting, stage of training, age of the subject, preferences for themes or characters including voices, songs, beeps, etc.) and/or may be based on data on wetting behavior and its progression over time collected within the device.

In other aspects of the present invention, the toilet training system includes an array of sensing articles that each provide different, or a combination of different, feedback modes. For example, one article may include a wetness sensing system 120 of the kind described herein whereas another article may include fading or appearing graphics, a temperature change mode, a tactile mode such vibratory or pressure modes, or a combination of any or all of these. The caregiver can select a different article with a different feedback mode to continue the training if the subject becomes accustomed to the current feedback mode being used.

In another aspect of the present invention, the feedback modes are classified as generally positive or pleasant feedback modes, or as generally negative or unpleasant feedback modes, although which feedback modes fall into which classifications may depend on individual feelings and preferences. In general, examples of positive or pleasant feedback modes include songs, nature sounds, murmurs, warming modes, and low volumes. Similarly, general examples of negative or unpleasant feedback modes include buzzes, beeps, tactile, cooling modes, and high volumes. Vocal or other verbal modes may fall into either classification. Wireless signals to a caregiver would generally be considered to be neutral. In one aspect of the present invention, a caregiver toilet training a subject selects one or the other class of feedback modes depending on the progress and goals of the toilet training, where a pleasant sound acts as positive reinforcement (e.g., for remaining dry), and an unpleasant sound acts as negative reinforcement (e.g., for wetting the article). Some subjects respond better to positive feedback modes, and some respond better to negative feedback modes.

In one aspect of the present invention, a signaling device 110 includes one type of feedback mode while a subject remains dry, and another type of feedback mode when an insult is occurring. A particular use of positive and negative feedback modes includes a signaling device 110 that rewards time that a subject remains dry with a positive feedback mode while notifying the subject of an occurring insult with a negative feedback mode, thus conditioning the child to remain dry and use proper toileting actions. In a specific example, the feedback mode for remaining dry is a caregiver's or character's voice encouraging the child, while the feedback mode for an insult is a subtle or less-than-subtle reminder from the same voice to take action. The negative feedback mode need not be negative or scolding in tone; the negative feedback mode may, for example, reassure the subject that the insult was okay and trying again is a part of learning In one aspect of the present invention, the caregiver chooses which class of feedback mode to use based on the responses of the subject and supplemented with guidance and information supplied with or separately from the articles 20 or signaling devices 110. The caregiver may select from different signaling devices 110 having different feedback modes, or between different feedback modes within the same signaling device 110.

In another aspect of the present invention, the signaling device 110 itself chooses the feedback modes. One way to accomplish this is to provide a signaling device 110 that includes a dynamic feedback system. A dynamic feedback system is capable of learning what approach works with a particular subject, and can use both positive and negative feedback modes as necessary to ensure toilet training progresses as well as it can.

The toilet training system includes the dynamic feedback system in which feedback modes change as a function of training conditions or duration of toilet training to provide appropriate variant feedback. This dynamic feedback system will help train the subject faster and will adjust if problems occur to help further increase training success. In a simple version of a dynamic feedback system, the system provides a positive feedback mode that transitions to a negative feedback mode if the positive feedback mode is not working to improve training times.

The dynamic feedback system improves toilet training progress by providing dynamic feedback responses based on either or both of the duration of training or the current status of training response. In various aspects of the present invention, this dynamic feedback is accomplished by an algorithm system or user-selectable conditions.

In a specific aspect of the present invention based on duration of training, when the subject first uses the toilet training system, the feedback mode provided is very positive and at low levels or volumes to allow the subject to become familiar with the system. Over subsequent days of training, this feedback mode can become more intense, such as with volume increases and/or feedback modes that transition from positive to negative. As toilet training improves and fewer insult events are detected, the feedback mode can then transition again to be more positive, such as by providing a positive feedback mode when no insult events are detected after a given time. This type of algorithm can function as a day counter to adjust the feedback modes based on number of days used and be calibrated on normal training durations. Additionally, a dynamic feedback system based on duration of training can be used to confirm the accomplishment of toilet training by reducing feedback modes. The reduction can confirm that toilet training has been accomplished by providing no feedback mode under certain conditions, yet still tracking whether insult events occur. This will help confirm that toilet training has been accomplished as a function of the subject and not as a function of reliance on dynamic feedback system.

Another specific aspect of the present invention is based on user-selectable conditions. This aspect is similar to that described above, whereas in this case the caregiver has control to influence the stage of training considered by the dynamic feedback system to provide the appropriate type of feedback mode based on the subject's progress. A smart algorithm or learning paradigm such as a neural network is designed such that, based on events recorded by the system such as a historical insult profile, the feedback mode used with the subject is adjusted to optimize the training based on the type of feedback mode that is effective with a given event pattern. The algorithm may also consider the duration the system has been used. The system can adjust the type of feedback mode used with each child. For example, if the system detects that recorded events indicate that a negative feedback mode is not providing training, the system will transition to provide positive a feedback mode and then will track progress to detect whether improvements occur based on the modified feedback type. Smart algorithms have been described for the similar application of temperature monitoring in U.S. Patent Application Publication No. U.S. 2005/0245839A1, published on Nov. 3, 2005, by Stivoric et al.

In any of the aspects of the present invention described herein, historical data can be gathered and processed by the signaling device 110 or by an external device in communication with the signaling device 110. For example, insult and other data can be downloaded from the signaling device 110 to a computer via BLUETOOTH wireless communication enabled devices, RFID, or a custom wetness sensor data reader that plugs into a USB or other port of the computer. Software on the computer uses data from the signaling device 110. The process may be similar to that employed with photo data and digital cameras. The computer can then analyze the data and formulate a recommendation for the caregiver, communicated to the caregiver directly, via another device, or via the signaling device 110. The combination of a small signaling device 110 and a larger display/audio device such as a laptop, cellular phone, or audio device such as an mp3 player makes the system more convenient and accessible for a caregiver.

The wetness sensing system 120 described herein allows a manufacturer to produce a variety of wetness sensing absorbent articles and signaling devices and package these together or separately. Each separate package may include a description of the condition intended to be addressed by that component of the wetness sensing system 120 (such as the wetness sensing absorbent article 20), a description of the primary function use of that signaling device 110, a description of and instructions as to the use of the entire wetness sensing system 120, or some combination thereof. The descriptions may be placed on the packaging, in the packaging, or some combination of both. The descriptions may allow a caregiver to become educated as to the conditions that typically dictate the use of a wetness sensing system 120, and the further conditions that may be associated with or experienced in conjunction with the use of a wetness sensing system 120. Such education allows a consumer to make informed decisions as to which signaling device or other associated products to purchase such that the consumer may assemble a customized wetness sensing absorbent article to address various conditions.

Consumer education may be further enhanced by providing indicia on the packaging to indicate various different but associated components of the wetness sensing system 120. The indicia may include graphic design features, text, branding, or any other suitable indicia. For example, all of the packages may exhibit similar graphic design components and branding to identify their association, yet have different coloring and illustrations to identify their differences. These indicia may help a consumer to quickly discern which products may be needed for a particular purpose.

In other words, the wetness sensing system 120 described herein allows a consumer to customize a wetness sensing absorbent article 20 on an as-needed basis to address whatever conditions the wearer may be experiencing without spending more every day for a wetness sensing absorbent article 20 that includes every signaling device and associated product. Consumers desire a high quality, consistent product at a good price with the ability to upgrade for certain circumstances.

In another aspect of the present invention, a consumer may be provided with flexibility in the use of the wetness sensing system 120 by including a plurality of signaling devices in a package with at least one wetness sensing absorbent article 20. In this aspect, the caregiver may select which signaling device to associate with the wetness sensing absorbent article 20 based on the situation in which the wetness sensing absorbent article 20 is to be used.

In another aspect of the invention, one or more wetness sensing absorbent articles 20 may be packaged and sold with a similar, dissimilar, related, or unrelated product. For example, a wetness sensing absorbent article 20 with a first signaling device 110 may be packaged and sold with a toilet training progress chart.

In various aspects, the wetness sensing system 120 may include informational items such as instructions in the use of the product and tips for toilet training, enuresis control, or incontinence control. As used herein, the term "informational item" refers to objects that are provided in addition to wetness sensing absorbent articles, are adapted to communicate information to the user and/or consumer of the wetness sensing absorbent article, and are associated with individual components of the wetness sensing system 120. Examples of informational items include cards, paper, electronic media, printing on the packaging, or other suitable media capable of storing and conveying information.

In various aspects, the informational items associated with the wetness sensing system components may be adapted to appeal to the specific category of user and/or purchaser to which the wetness sensing absorbent article is adapted. The informational items may be adapted, for example, by providing information likely to be of interest to a given category of user and/or purchaser.

For example, a wetness sensing absorbent article may be adapted for use by a caregiver for toilet training purposes. An informational item may be associated with the wetness sensing absorbent article that is adapted to interest caregivers. For example, the informational item may be a card containing information or instructions about children's health and hygiene, such as sleep habits, thumb sucking, teething, skin health, toilet training; questions to ask a child; jokes; and the like, and combinations thereof. The informational item may additionally or alternatively include addresses for web sites available on the Internet. The web sites may contain information related to issues of interest for caregivers and users of wetness sensing absorbent articles.

The informational item may additionally or alternatively include addresses for web sites available on the Internet, audio recorded information that can be played back by the signaling device 110, recorded information that can be played back when the signaling device 110 is in communication with a computer, and information delivered through the Internet when the signaling device 110 is in communication with the Internet.

The informational item may additionally or alternatively include information describing activities that are suitable for caregivers and users of wetness sensing absorbent articles. The activities may be adapted for a child at a specific age, size, and/or stage of development. For example, the activities may be adapted to promote interaction between the child and the caregiver.

The informational item may additionally or alternatively include information describing the benefits to be derived from using the wetness sensing system 120. This informational item would be part of a promotional plan emphasizing the customizability of the wetness sensing system 120 for the benefit of the consumer, caregiver, and/or user. This informational item would both explain the use of the various components of the wetness sensing system 120 as well as presenting the additional components that may be available and the various combinations that are possible to achieve different goals.

Use of products such as those described herein provides an opportunity for training beyond that provided by products that simply notify a caregiver that a subject has previously experienced an insult. Providing notification or another feedback mode in a timely manner, particularly one that is contemporaneous with the insult, provides a training opportunity at its most valuable timing. The present invention provides a caregiver with the tools to detect an insult in a timely manner to allow intervention, and then intervening to provide training. Training using these tools is described using toilet training as an example, but are equally applicable to other situations such as incontinence training, enuresis training, and pre-toilet-training stages as well.

The caregiver is provided with instructions, guidance, and information with respect to the actions to follow to best use an insult as an opportunity to toilet train a subject. The caregiver is instructed to respond to an insult while the insult is occurring or as soon as possible thereafter. The caregiver and subject may respond to a feedback mode by discussing the physical sensations sensed by the subject before the insult occurs and while the insult is occurring, such physical sensations to include sensations of pressure, temperature and pressure changes, wetness, and any other appropriate sensations. The caregiver and subject may also respond to a feedback mode by discussing the relation between the physical sensations and the imminence of the insult. For example, the caregiver may point out the sensations experienced by the subject just prior to the insult and help the subject to associate those sensations with the imminence of an insult.

The caregiver and subject may also respond to a feedback mode by making sure the subject is taken to a bathroom and by discussing the relationship between the insult, the bathroom, and perhaps the feedback mode. The caregiver and subject may also respond to a feedback mode by making sure the subject is positioned on a toilet or other appropriate receptacle and by discussing the relationship between the insult, the toilet or other receptacle, and perhaps the feedback mode. The caregiver may also respond to a feedback mode by encouraging the subject to produce an insult while positioned on the toilet or other receptacle, again discussing the relationship between the insult, the toilet or other receptacle, and perhaps the feedback mode. The caregiver may also respond to a feedback mode by recognizing any positive actions taken by the subject to encourage the subject to perform additional positive acts.

Toilet training may be further enhanced by giving the caregiver instructions and tools with respect to tracking and assessing the toilet training progress of the subject. Understanding the progress or lack of progress being made by the subject allows the caregiver to adjust the toilet training to improve progress, as described herein. The caregiver may track and assess toilet training progress independent of the signaling device, or the signaling device may be configured to store data for tracking and assessing progress toward the achievement of toilet training.

Using products such as those described herein, the caregiver can use a wetness sensing system that includes a plurality of feedback modes. The caregiver, in acquiring such products, can also acquire instructions and guidance in how to use the plurality of feedback modes if toilet training progress slows. One reason for a slowing of toilet training progress is that the subject becomes accustomed or habituated to a feedback mode that is used. With the products described herein, the caregiver may select different feedback modes to overcome this accustomization and to allow toilet training to progress at a faster rate. As further described above and in various aspects of the present invention, the plurality of feedback modes may include a sound, a verbal cue, a lighting cue, a wireless signal, a fading graphic, an appearing graphic, a temperature-change member, and/or a tactile member such as a vibratory or pressure member. It should be noted that the feedback mode can be adjusted based on whether caregiver is responding so that the caregiver does not habituate to a particular feedback mode. Information can be provided to help a caregiver recognize the potential for caregiver habituation. The dynamic feedback system can be programmed to alter the feedback mode when it recognizes that the response time by the caregiver has slowed.

In another aspect of the present invention, toilet training may be further enhanced by giving the caregiver instructions and tools with respect to using positive and negative feedback modes. The caregiver can be given instructions and guidance in how and when to select either positive or negative feedback modes based on the progress of toilet training and the actions and reactions of the subject. The proper selection for a given subject allows toilet training to progress at a faster rate. As examples that are described further above, the positive feedback mode or indication may be a song or a verbal prompt, and the negative feedback mode or indication may be an unpleasant sound.

In another aspect of the present invention, toilet training may be further enhanced by giving the caregiver instructions and tools with respect to using a signaling device 110 that includes a feedback mode that an insult has not occurred. Encouraging the subject to remain dry can allow toilet training to progress at a faster rate.

To be clear, and in other aspects of the present invention, toilet training may be further enhanced by giving the caregiver instructions and tools with respect to using a signaling device 110 or a wetness sensing system 120 that includes any of the devices, information, instructions, and/or schemes described herein, including the dynamic feedback system. The caregiver may choose between many options and varieties of wetness sensing systems, indications, feedback modes, selectability, and automation. Use of such devices, information, instructions, and/or schemes allows toilet training to progress at a faster rate.

In another aspect of the present invention, the receiver 114 provides feedback to the caregiver or subject. For use in conjunction with efforts to stem enuresis, for example, the receiver 114 may indicate the number of dry nights and the status of an alarm being set, or may include an alternate visual indicator. This aspect may involve a wireless query of the transmitter 112 to ensure the transmitter has not detected an insult in a given amount of time.

These and other modifications and variations to the present invention may be practiced by those of ordinary skill in the art, without departing from the spirit and scope of the present invention, which is more particularly set forth in the appended claims. In addition, it should be understood that aspects of the various aspects of the present invention may be interchanged either in whole or in part. Furthermore, those of ordinary skill in the art will appreciate that the foregoing description is by way of example only, and is not intended to limit the invention so further described in such appended claims.

What is claimed:
1. A toilet training system comprising:
a disposable absorbent article including a first wetness sensor;
a signaling device adapted to be removably attachable to the disposable absorbent article, adapted to communicate with the first wetness sensor, providing a first feedback mode of a wetness state of the disposable absorbent article and providing a second feedback mode of the wetness state of the disposable absorbent article, wherein the second feedback mode is different from the first feedback mode, and wherein the device is selectable between the first and second feedback modes.

2. The system of claim 1, wherein one of the first and second feedback mode is a negative feedback mode, and wherein the other of the first and second feedback mode is a positive feedback mode.

3. The system of claim 1, wherein a caregiver selects between the first and second feedback modes.

4. The system of claim 1, wherein the device is adapted to select between the first and second feedback modes.

5. The system of claim 1, wherein selecting between the first and second feedback modes considers a response of a user of the toilet training system.

6. The system of claim 1, wherein selecting between the first and second feedback modes considers a historical insult profile.

7. The system of claim 1, wherein selecting between the first and second feedback modes considers a duration of a dry wetness state.

8. The system of claim 1, wherein the disposable absorbent article further includes a second wetness sensor.

9. The system of claim 8, wherein the second wetness sensor is one of a wireless signal, a fading graphic, an appearing graphic, a temperature-change member, and a tactile member.

10. A toilet training system comprising:
a disposable absorbent article including a wetness sensor; and
a signaling device adapted to communicate with the wetness sensor, wherein the signaling device includes a dynamic feedback mode system.

11. The system of claim 10, wherein the dynamic feedback mode system selects between a plurality of feedback modes.

12. The system of claim 11, wherein the plurality of feedback modes includes positive and negative feedback modes.

13. The system of claim 10, wherein the signaling device is adapted to allow a user to select between positive and negative feedback modes, and wherein the dynamic feedback mode system selects between a plurality of feedback modes within such selected positive or negative feedback mode.

14. The system of claim 10, wherein the dynamic feedback mode system is adapted to select between a plurality of feedback modes on a basis that includes a duration of toilet training.

15. The system of claim 10, wherein the dynamic feedback mode system is adapted to select a first feedback mode, evaluate toilet training progress, and transition to a second feedback mode.

16. The system of claim 10, wherein the dynamic feedback mode system includes an algorithm.

17. The system of claim 10, wherein the dynamic feedback mode system includes a historical insult profile.

18. The system of claim 17, wherein the dynamic feedback system is adapted to select between a plurality of feedback modes on a basis that includes the historical insult profile.

19. The system of claim 10, wherein the dynamic feedback mode system includes the use of a neural network.

* * * * *